(12) United States Patent
Forstner et al.

(10) Patent No.: US 9,045,449 B2
(45) Date of Patent: Jun. 2, 2015

(54) METHOD FOR THE MANUFACTURE OF FURAN COMPOUNDS FOR RENEWABLE PRIMARY PRODUCTS

(71) Applicant: FRAUNHOFER-GESELLSCHAFT ZUR FÖRDERUNG, Munich (DE)

(72) Inventors: Jochen Forstner, Simmozheim (DE); Rainer Schweppe, Karlsruhe (DE); Gerd Unkelbach, Berg (DE); Klemens Flick, Waldsee (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 104 days.

(21) Appl. No.: 13/629,951

(22) Filed: Sep. 28, 2012

(65) Prior Publication Data

US 2013/0085285 A1    Apr. 4, 2013

(30) Foreign Application Priority Data

Sep. 30, 2011   (EP) .................................... 11007974

(51) Int. Cl.
  *C07D 307/48*  (2006.01)
  *C07D 307/46*  (2006.01)
  *C07D 307/50*  (2006.01)

(52) U.S. Cl.
  CPC ............ *C07D 307/48* (2013.01); *C07D 307/46* (2013.01); *C07D 307/50* (2013.01)

(58) Field of Classification Search
  CPC .................................................. C07D 307/48
  USPC ....................................................... 549/488
  See application file for complete search history.

(56) References Cited

U.S. PATENT DOCUMENTS

| 8,053,615 B2 | 11/2011 | Cortright |
| 8,697,893 B2 | 4/2014 | McNeff et al. |
| 2010/0191004 A1 | 7/2010 | McNeff et al. |

FOREIGN PATENT DOCUMENTS

| CN | 1974382 A | 6/2007 |
| CN | 101787006 A | 7/2010 |
| DE | 1191734 B | 4/1965 |
| DE | 19619075 A1 | 11/1997 |
| EP | 2574609 A1 | 4/2013 |
| KR | 1020100060301 A | 6/2010 |
| KR | 101064664 B1 | 9/2011 |
| WO | 2007104515 A1 | 9/2007 |
| WO | WO2007/104515 A1 * | 9/2007 |
| WO | WO2008/054804 A2 * | 5/2008 |
| WO | 2010030196 A1 | 3/2010 |
| WO | 2010075437 A2 | 7/2010 |
| WO | 2011063500 A1 | 6/2011 |
| WO | 2012050625 A2 | 4/2012 |

OTHER PUBLICATIONS

Chareonlimkun, Champreda, V.A., et al., "Reactions of C5 and C6-sugars, cellulose, and lignocellulose under hot compresses water (HCW) in the presence of heterogenouse acid catalysts", Fuel, Oct. 1, 2010 IPC Science and Technology Press, Guildford, GB, vol. 89, Nr.10, pp. 2873-2880, (2010).
McNeff, C.V., et al., "Continuous production of 5-hydroxymethylfurfural from simple and complex carbohydrates", Applied Catalysts A: General, Aug, 20, 2010, Elsevier Science Amsterdam, NL, vol. 384, Nr:1-2, pp. 65-69, (2010).
European Extended Search Report, dated Jan. 31, 2013.
German Office Action dated Jun. 18, 2012.
Chareonlimkun, A., et al., "Reactions of C5 and C6-sugars, cellulose, and lignocellulose under hot compressed water (HCW) in the presence of heterogenous acid catalysts" Fuel 89 (2010) 2873-2880.
McNeff, Clayton V., et al., "Continuous production of 5-hydroxymethylfurfural from simple and complex carbohydrates", Applied Catalysts A: General 384 (2010) 65-69.
European Office Action dated Jan. 5, 2015.

* cited by examiner

*Primary Examiner* — Taofiq A Solola
(74) *Attorney, Agent, or Firm* — Tarolli, Sunhdeim, Covell & Tummino LLP

(57) ABSTRACT

Method for the manufacture of furan compounds by using a heterogeneous catalyst in aqueous solution.

8 Claims, 3 Drawing Sheets

Figure 1: Synthesis installation for continuous mode
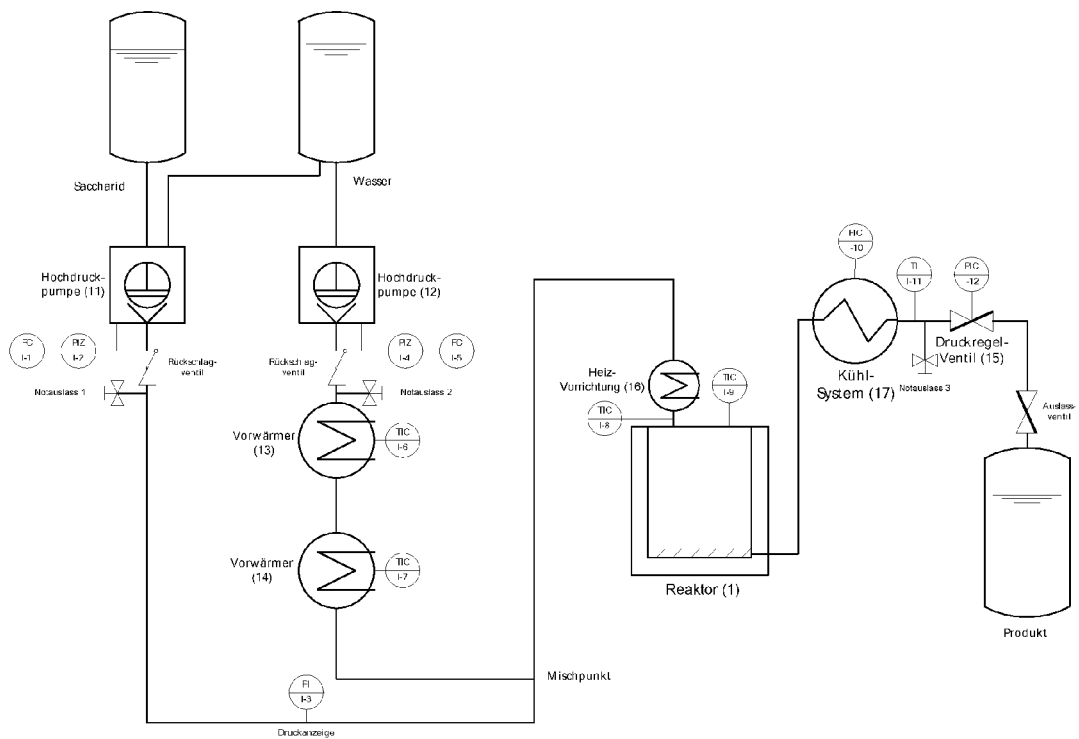

Figure 2: Influence of calcination temperature on product yield of the $AlPO_4$ catalyst system
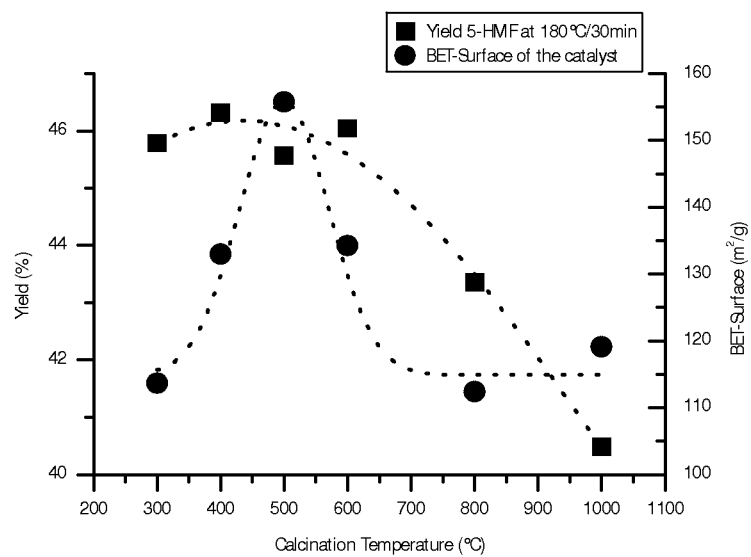

Figure 3: Influence on the catalyst activity and the pH of the product solution upon repeated use of a zirconium phosphate catalyst
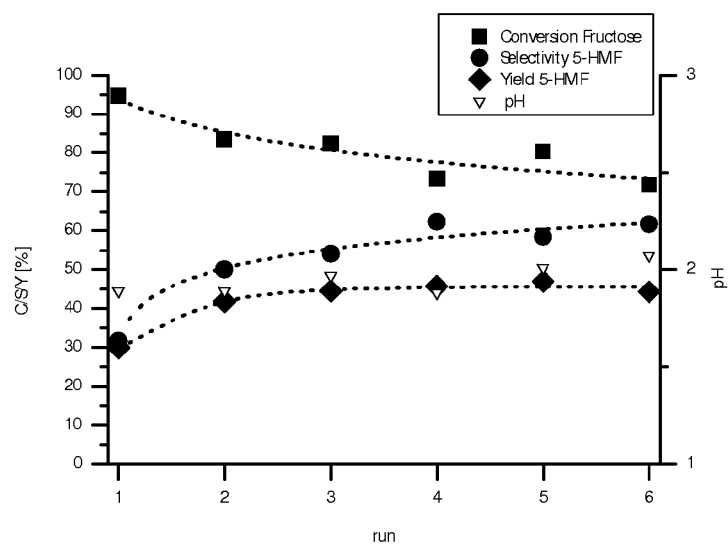

METHOD FOR THE MANUFACTURE OF FURAN COMPOUNDS FOR RENEWABLE PRIMARY PRODUCTS

This application claims priority from European Patent Application No. 11 007 974.6, filed Sep. 30, 2011, the subject matter of which is incorporated herein by reference in its entirety.

The present invention relates to the manufacture of furan compounds from renewable primary products. In this respect, the invention describes a simple and economic method for the manufacture of furan compounds in the presence of a heterogeneous catalyst. Furthermore, the present invention relates to a heterogeneous catalyst as well as a method for its production. An embodiment of the present invention describes the manufacture of furfural and 5-hydroxymethylfurfural in the presence of a heterogeneous catalyst system from an aqueous solution.

BACKGROUND OF THE INVENTION

Scarcity and increasing costs of fossil fuels have caused increased interest in sustainable synthesis strategies. In this respect, synthesis of chemical basic materials which typically are obtained from petrochemical refinement, are of special interest. Significant efforts have been taken for developing alternative synthesis strategies in order to meet the needs of the chemical industry also in the future. An especially successful concept in this respect is biorefinement. "biorefinement" refers to a technical method for purifying, refining, separating and/or concentrating of individual raw materials from a biomass, wherein renewable primary products are considered a "biomass". On the other hand, fossil energy sources obtained from biomass are not considered renewable primary products. Biomass generally contains about 35 to 50% cellulose, 25 to 30% hemicellulose and 25 to 30% lignin. Hemicellulose is a general term for mixtures of polysaccharides present in herbal biomass. By way of biorefinement saccharide such as glucose, xylose and fructose can be obtained.

The present invention relates to the manufacture of furan compounds from saccharides. In this respect the invention describes a simple and costs effective method for the manufacture of furan compounds in the presence of a heterogeneous catalyst. Furan compounds are of special interest, since they are valuable intermediates in the manufacture of polymers, solvents, pharmaceutical products, fine chemicals, fuels, fertilizers and herbicides. In most cases there are high requirements regarding purity of the required furan compounds.

Manufacture of furan compounds from renewable primary products is known and has been put into technical practice. The manufacture of furan compounds, especially of furfural and 5-hydroxymethylfurfural is, however, difficult, since consecutive reactions lead to various degradation products. In known methods for the manufacture of furan compounds homogeneous catalysts are used. "Homogeneous catalysts" are catalyst systems in which the catalyst and the educt are present in the same phase. In the known methods inorganic acids are normally used as catalysts. For example, the manufacture of furan compounds in the presence of homogeneous acids, especially inorganic homogeneous acids such as sulphuric acid, phosphoric acid or hydrochloride acid, is described in "Reactions of d-fructose in water at temperatures up to 400° C. and pressures up to 100 MPa, Aida T. M. et al., *Journal of Supercritical Fluids* 2007, 42(1), 110-119.

In view of the use of homogeneous catalysts a laborious and cost intensive work-up is necessary. For example, acids first have to be neutralized in order to stop the reaction and further work-up is made possible. In addition, in known methods organic solvents, ionic fluids or supercritical fluids are used, which further complicates work-up an increases production costs. In particular, the use of organic solvents and other adjuvant has a negative effect on the purity of the obtained furan compounds.

Therefore, there is a need for new catalysts, catalyst systems or reaction systems for improving the manufacture of furan compounds. In this respect it is of special interest to optimized the manufacturing process in order to achieve a lower product prize.

BRIEF DESCRIPTION OF THE INVENTION

The object underlying the invention is the provision of an improved method for the manufacture of furan compounds, wherein educts are used in the method which can be isolated from renewable primary products. The term "educt" refers to a starting material subjected to a chemical reaction in order to obtain a product therefrom.

The object is solved using the features of the independent claims. Advantageous embodiments of the invention are described in the dependent claims.

The invention relates to a simple and cost effective method for the manufacture of furan compounds in the presence of at least one heterogeneous catalyst. Preferably the manufacture of furan compounds is carried out in aqueous solution. The term "heterogeneous catalyst" refers to catalyst systems in which catalyst and educt are present in different phases. In this respect, the term "heterogeneous catalyst" comprises also catalyst systems which exclusively consist of the compound having catalytic activity as well as catalyst systems containing further components apart from the compound having catalytic activity as in case of supported catalysts.

In one embodiment the inventive method is used for the manufacture of furfural and 5-hydroxymethylfurfural.

The inventive method comprises the production of an educt solution, preferably an aqueous educt solution. This educt solution contains an alcohol or polyalcohol, preferably at least one saccharide, in particular xylose and/or fructose. In other words, the inventive method comprises the provision of at least one saccharide, preferably xylose and/or fructose, especially in the form of an aqueous solution. Subsequently a heterogeneous catalyst is added to the educt solution and the reaction mixture is heated for 5 to 240 minutes to 140 to 250° C., especially for 10 to 60 minutes to 150 to 200° C. This range is of special importance, since in case of shorter reaction times and/or lower temperatures satisfying turnover numbers and yields are not obtained and in case of longer reaction times and/or higher temperatures significant decomposition of the reaction products occurs. Subsequently the heterogeneous catalyst is removed from the reaction mixture by means of filtration or other methods for separating heterogeneous mixtures and the product solution preferably containing a furan compound, especially furfural or 5-hydroxymethylfurfural is separated.

The invention further relates to a heterogeneous catalyst and the manufacture thereof as well as the use of the catalyst and a group of catalysts in the inventive method for dehydrating alcohols or polyalcohols, especially for the manufacture of furan compounds, preferably furfural or 5-hydroxymethylfurfural. The inventive heterogeneous catalyst comprises at least a metal and/or semimetal and/or transition metal. In a preferred embodiment, the heterogeneous catalyst comprises a metal oxide and/or transition metal oxide, preferably $TiO_2$, $Cr_2O_3$ and/or $ZrO_2$. In a further preferred embodiment the heterogeneous catalyst comprises a metal phosphate and/or transition metal phosphate, preferably $FePO_4$, $Zr_3(PO_4)_4$, $BPO_4$, $AlPO_4$ and/or $GaPO_4$ or mixtures thereof. In a special embodiment the metal oxide and/or transition metal oxide is further treated with an acid so that the surface of the metal oxide and/or transition metal oxide is modified, in particular the surface structure and the surface activity is modified. In an inventive embodiment $TiO_2$, $Cr_2O_3$ and/or $ZrO_2$ are treated with $H_2SO_4$ so that sulphated $TiO_2$, $Cr_2O_3$ and/or $ZrO_2$ are obtained, especially sulphated $TiO_2$ and $ZrO_2$. In an embodiment the inventive heterogeneous catalyst has a specific surface in a range of 75 to 250 $m^2/g$, preferably 100 to 200 $m^2/g$, particularly 130 to 180 $m^2/g$.

Different methods for the manufacture of the inventive heterogeneous catalysts are conceivable. In most cases the manufacture is carried out by means of a corresponding precursor compound. In one embodiment the precursor compound is at first broken up and is subsequently heated in a suitable reaction medium. The precursor compound is preferably completely dissolved here and the catalyst is precipitated after completion of the reaction whereby a heterogeneous catalyst is obtained. In a further embodiment the catalyst is precipitated in the presence of a suitable support material. The term "support material" refers to materials that are mixed or coated with catalyst so that a solid catalyst system is obtained. Preferably the support material is a porous material.

The heterogeneous catalyst is subsequently calcinated. The term "calcination" refers to heating the material in order to dehydrate it. Calcination is carried out in a range of 200 to 1200° C. and over a period of 1 to 10 hours.

In a preferred embodiment the inventive method for the manufacture of a furan compound is carried out in aqueous solution in the presence of a catalyst the manufacture thereof including a calcination step at 200 to 1000° C., preferably 400 to 1000° C., particularly 400 to 600° C.

In a further preferred embodiment, the catalyst or the catalyst system is dried. Drying occurs in a temperature range of 50° C. to 350° C., preferably 75° C. to 250° C., particularly 100° C. to 200° C. over a period of 1 to 48 hours, preferably 1 to 24, particularly 12 to 24. In an especially preferred embodiment the drying is carried out in addition to calcinating particularly before calcinating.

The inventive heterogeneous catalyst is a part of the inventive method for the manufacture of furan compounds, especially furfural and 5-hydroxymethylfurfural, wherein the manufacture is preferably carried out in aqueous solution.

DESCRIPTION OF THE FIGURES

FIG. 1 shows as schematical presentation of a synthesis reactor capable of continuous use.

FIG. 2 shows the influence of the calcinating temperature on product yield and specific catalyst surface.

FIG. 3 show the influence on catalyst activity and pH of the product solution in case of repeated use of a zirconium phosphate catalyst.

DETAILED DESCRIPTION OF THE INVENTION

The invention relates to a simple and cost effective method for the manufacture of furan compounds from aqueous solution in the presence of a heterogeneous catalyst. In particular, the invention relates to a method for the manufacture of furan compounds from an aqueous saccharide solution. In preferred embodiment of the invention, the saccharide used for providing the aqueous saccharide solution is obtained by means of a biorefinement method. In a further preferred embodiment the saccharide is directly obtained from a biogenic source.

Biorefinement is a complex and integrated system of processes and installations in which biomass is converted to a variety of products which is related to the concept of petrochemical refinement. A biorefinement process relates to the application of efficiency and logistics of fossil based chemical industry and commerce wherein not fossil starting materials such as petroleum or petroleum gas but bio mass of any composition is converted.

A special embodiment of the invention relates to a method for the manufacture of furfural from an aqueous xylose solution in the presence of the heterogeneous catalyst. A further special embodiment of the invention relates to a method for the manufacture of 5-hydroxymethylfurfural from an aqueous fructose solution in the presence of a heterogeneous catalyst. A further special embodiment of the invention relates to a method for the manufacture of furfural and/or 5-hydroxymethylfurfural from an aqueous xylose and/or fructose solution in the presence of a heterogeneous catalyst. In particular, xylose and fructose can represent intermediates in the inventive method which form by means of isomerisation from the alcohols or polyalcohols used as the educt, wherein isomerisation refers to a process in which an isomer is formed by means of intermolecular conversations of a chemical compound. In a special embodiment xylose and/or fructose is obtained in the inventive method from cellulose, especially saccharose, preferably glucose.

The inventive method comprises at least the following steps:

(a) providing an educt solution, in particular an aqueous educt solution.

The educt solution contains at least an alcohol or polyalcohol, preferably at least a saccharide, selected from the group consisting of glyceraldehyde, threose, erythrose, ribose, arabinose, xylose, lynose, allose, altrose, glucose, mannose, gulose, idose, galactose, talose, dihydroxyacetone, erythrolose, ribulose, xylulose, psicose, fructose, sorbose and tagatose, in particular xylose or fructose. Preferably an educt solution is provided which comprises an alcohol or polyalcohol content of 1 to 50 wt-%, preferably 1 to 25 wt-%, particularly 1 to 10 wt-%.

(b) adding a heterogeneous catalyst.

A heterogeneous catalyst is added to the educt solution. In a preferred embodiment the heterogeneous catalyst comprises a metal oxide and/or semimetal oxide and/or transition metal oxide. Preferred are metals of main group III and transition metals of subgroup IV of the periodic system, especially Al, Ti and Zr. In a further preferred embodiment the heterogeneous catalyst comprises a metal phosphate and/or semimetal phosphate and/or transition metal phosphate; preferred are metals of main group III and transition metals of subgroup IV and VIII of the periodic system, especially Fe, Zr, B, Al and Ga. In an inventive embodiment, the heterogeneous catalyst is added in an amount so that the weight ratio of catalyst and educt is in a range of between 1:50 and 1:2, preferably in range between 1:10 and 1:5. In a special embodiment the catalyst is added in an amount so that the weight ratio between catalyst and educt is 1:25, preferably 1:10, particularly 1:5.

(c) heating of the reaction solution.

The reaction mixture is heated for a period of from 1 to 240 minutes, preferably from 1 to 120 minutes, particularly 10 to 60 minutes to 100 to 250° C., preferably 150 to 200° C., particularly 160 to 180° C. For the manufacture of furfural a reaction period of 60 minutes at 160° C. is especially preferred and for the manufacture of 5-hydroxymethylfurfural a reaction period of 30 minutes at 180° C. is preferred. For the manufacture of furfural from xylose in the presence of AlPO$_4$ a reaction period of 30 minutes at 200° C. is especially suitable.

(d) separating the heterogeneous catalyst

Subsequently the heterogeneous catalyst is removed from the reaction mixture. In a special embodiment the reaction mixture is cooled to room temperature before the heterogeneous catalyst is removed from the reaction mixture. Various techniques are known for removing a heterogeneous material, especially a heterogeneous catalyst, from a reaction mixture, which may be used in the context of the invention. Especially preferred is the separation of the catalyst by means of filtration or centrifugation. The heterogeneous catalyst can easily be removed from the reaction mixture so that the reaction time can be controlled well and the process parameters can be adjusted exactly.

(e) isolating the products

Finally, the product, preferably a furan compound, especially furfural or 5-hydroxymethylfurfural, is isolated from the reaction solution. Various techniques are also known here which can be used in the context of the invention. In one embodiment isolation of the furan compound, especially of furfural or 5-hydroxymethylfurfural form the reaction solution, especially the aqueous reaction solution, is carried out by means of a simple extraction step using a suitable solvent or solvent mixture. In a special embodiment, the solvent or solvent mixture comprises an organic solvent, preferably a ketone and/or an alcohol, particularly an aromatic ketone and/or an aromatic alcohol.

In a further embodiment the isolation of the product, preferably a furan compound, particularly furfural or 5-hydroxymethylfurfural, from the reaction solution is carried out by means of distillation and/or rectification. In an especially preferred embodiment the isolation of the product comprises at least two distillation steps, wherein in the first distillation step impurities having a lower boiling point as the target compound are removed via the head of the distillation or rectification device, and in a second distillation step impurities having a higher boiling temperature as the target compound are removed via the bottom of the distillation or rectification device. The second distillation step is preferably carried out in a second distillation or rectification device.

Distillation and/or rectification can be carried out alternatively or additionally to extraction.

In an embodiment of the invention the furan compound is separated from the product solution in a first process step by means of extraction with a suitable solvent or solvent mixture. The solvent or solvent mixture comprises an organic solvent, preferably a ketone and/or an alcohol particularly and aromatic ketone and/or aromatic alcohol. The furan compound is subsequently isolated in a second process step by means of distillation and/or rectification.

In a further preferred embodiment the furan compound is separated in a first distillation step via the bottom and subsequently in a second distillation step via the head of a distillation or rectification device. In this way furan compounds of high purity can be obtained. In this respect the first and the second distillation step can be carried out in the same or in different distillation or rectification devices.

The method according to the invention is particularly characterized in that the reaction time can be significantly reduced compared to known methods and simultaneously turnover rates and yields can be increased. The method of the invention furthermore can be carried out at relatively high temperatures without a significant catalytic and/or thermic degradation of the products, particularly to humins and organic acids, taking place. While known methods for the manufacture of furan compounds, especially furfural or 5-hydroxymethylfurfural usually employ a reaction time of several hours, the reaction time of the method according to the invention is in the range of 1 to 120 minutes, particularly 1 to 60 minutes, further preferably 10 to 60 minutes, especially 30 to 60 minutes.

A further decisive advantage of the method of the invention over known methods is that no organic solvents, ionic liquids, supercritical fluids or other adjuvants such as phase adjuvants, which require an additional work-up step, are employed. In the heterogeneously catalyzed method products of higher purity are obtained compared to homogeneously catalysed methods.

The method of the invention can be carried out in batch mode as well as in continuous mode. Batch mode is preferably carried out in a steal autoclave, while continuous mode is preferably carried out in an flow pipe reactor or a stirrer vessel reactor in continuous mode. It has been shown that the use of supported catalysts is especially suitable for use in flow pipe reactors, while for the use in stirrer vessel reactors in continuous mode catalysts in particle form are especially suitable. Separation of the heterogeneous catalyst can be carried out in batch mode by means of simple filtration, while in continuous mode recovery of the catalyst is preferably carried out by means of sinter metal filters, inert packed beads, fine mashed stainless steal filters or restrictions in cross section.

According to the embodiment shown in FIG. 1 the synthesis installation in continuous mode comprises at least a high pressure pump, at least a pre-heater for heating the reaction medium, particularly water, a reactor, particularly a heated reactor, at least a cooling system, particularly a liquid/liquid heat exchanger and at least a pressure control valve.

The method according to the invention comprises both single strand as well as multi strand methods, wherein the term "single strand method" refers to a method having one high pressure pump, while multi strand methods are methods having more than one high pressure pump, especially methods having more than one high pressure pump and at least one mixing unit.

Furthermore, the present invention refers to a heterogeneous catalyst and its manufacture, as well as the use of the catalyst in a method for dehydrating alcohols or polyalcohols, particularly for the manufacture of furan compounds in aqueous solution. In this respect the catalyst according to the invention forms a significant part of the method of the invention for the manufacture of furan compounds, especially for the manufacture of furfural or 5-hydroxymethylfurfural. The heterogeneous catalyst of the invention comprises at least one metal and/or semimetal and/or transition metal, preferably selected from main group III or subgroup IV and VIII of the periodic system of elements. The metal and/or semimetal and/or transition metal in this respect is preferably a trivalent, tetravalent or pentavalent metal cation.

In a preferred embodiment, the heterogeneous catalyst comprises a metal oxide or/semimetal oxide and/or transition metal oxide, preferably $B_2O_3$, $Al_2O_3$, $TiO_2$, $ZrO_2$, FeO, $Fe_2O_3$, $Fe_3O_4$ and/or mixtures thereof.

In a further preferred embodiment, the heterogeneous catalyst comprises a metal phosphate and/or semimetal phosphate and/or transition metal phosphate, preferably $BPO_4$, $AlPO_4$, $GaPO_4$, $Zr_3(PO_4)_4$, $Ti_3(PO_4)_4$, $FePO_4$ and/or mixtures thereof.

In a further preferred embodiment the heterogeneous catalyst comprises at least one mixed compound, preferably mixed compounds of $SiO_2$ and $Al_2O_3$, especially aluminosilicate.

The heterogeneous catalyst preferably has a specific surface lower than 200 $m^2/g$, particularly lower than 160 $m^2/g$. In preferred embodiment the heterogeneous catalyst has a specific surface in the range of 100 to 200 $m^2/g$, particularly 130 to 180 $m^2/g$.

The catalysts of the invention are suitable for dehydrating alcohols and polyalcohols. In particular, the catalyst according to the invention are suitable for dehydrating aldoses and ketoses as well as polymers thereof and products derivable therefrom. In this respect dehydration of saccharides is of special importance. In a preferred embodiment the catalyst has a low solubility product in water which forms the preferred reaction medium. Especially preferred are oxide containing and/or phosphate-containing catalysts, wherein the oxide and the phosphate form the anion, and the decomposition of the catalytically active material in contact with water occurs very slowly due to the low solubility.

Several methods for the manufacture of a heterogeneous catalyst according to the invention are conceivable. In most cases the manufacture of the catalyst is carried out by means of corresponding precursor compounds and their precursors.

One embodiment of the method of the invention comprises at least the following steps:
 (a) providing a solution of a compound containing metal, semimetal or transition metal.

Preferably precursor compounds or their precursors are used distributed in a suitable solvent, which preferably contains an acid, particularly phosphoric acid. In preferred embodiment the metal, semimetal or transition metal compound is crushed, so that a fine powder is obtained which subsequently is distributed in a suitable solvent. In a special embodiment the fine powder is distributed in a molecularly dispersed way so that a homogeneous solution is obtained.
 (b) heating the solution containing metal, semimetal or transition metal.

Preferably the solution is heated to the boiling point of the employed solvent. Preferably the metal, semimetal or transition metal compound is completely dissolved at the latest here.
 (c) precipitating and isolating the catalyst The catalyst is precipitated by adding the suitable reagent or by cooling the solution.

In a preferred embodiment the catalyst is precipitated in the presence of a suitable support material. Typical support materials are carbon black, silica gel, zeolites or metal oxides. In a further preferred embodiment the catalyst is dipped into a suitable acid, preferably $H_2SO_4$, and impregnated, in this connection the term impregnating refers to a surface treatment of the catalyst. By treating the surface of the catalyst with $H_2SO_4$ the surface of the catalyst is sulphated.

The catalyst is subsequently isolated from the solution using known methods, preferably a filtration method.
 (d) calcinating the catalyst.

The heterogeneous catalyst is subsequently calcinated. Calcination is carried out in a range from 200 to 1200° C., preferably in a range from 200 to 1000° C., especially preferably in a range of 400 to 1000° C. In preferred embodiment calcination is carried out in a range of 400 to 600° C., particularly 450 to 550° C. By means of calcination liquid residues are removed and the catalyst is activated. As shown in FIG. 2 the temperature during calcination has a decisive influence on the activity of the catalyst and the surface thereof.

Optionally the heterogeneous catalyst is dried. Drying is carried out in a temperature range of 75° C. to 250° C., preferably 100° C. to 200° C., particularly 105° C. over a period of 1 to 48 hours, preferably 1 to 24, particularly 12 to 24. In a preferred embodiment drying is carried out in addition to calcinating, particularly before calcinating.

In an embodiment of the invention the precursor compounds are metal oxides and/or transition metal oxides and/or semimetal oxides. In preferred embodiment, the precursor compounds are metal chlorides and/or transition metal chlorides and/or semimetal chlorides.

In a further preferred embodiment of the invention the precursor compounds are metal nitrates and/or transition metal nitrates and/or semimetal nitrates.

In an embodiment aluminum phosphate is produced from the precursor compound aluminum nitrate. In this respect the aluminum nitrate is at first dissolved in water and subsequently converted into aluminum phosphate by adding $H_3PO_4$. The reaction solution is subsequently neutralized by adding a suitable base, preferably ammonia, and aluminum phosphate is precipitated.

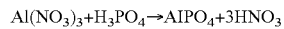

preferably

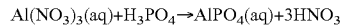

Precursors of the precursor compounds may be hydroxides. The metal hydroxides and/or transition metal hydroxides and/or semimetal hydroxides may be converted into corresponding chlorides and nitrates in the presence of suitable acids, preferably suitable inorganic acids, particularly HCl or $HNO_3$.

In an embodiment aluminum phosphate is produced from the precursor aluminum hydroxide. In this respect aluminum hydroxide is at first converted to aluminum nitrate by adding $HNO_3$. Subsequently aluminum nitrate is converted to aluminum phosphate by adding $H_3PO_4$. The reaction solution is subsequently neutralized by adding a suitable base, preferably ammonia, and the aluminum phosphate is precipitated.

$$Al(OH)_3 + 3HNO_3 \rightarrow Al(NO_3)_3 + 3H_2O$$

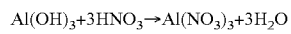

preferably

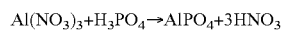

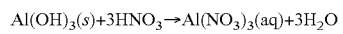

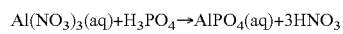

The manufacture of catalysts of the invention from metal chlorides and/or transition metal chlorides and/or semimetal chlorides is carried out analogously. In this respect the metal hydroxide and/or transition metal hydroxide and/or semimetal hydroxide is at first converted into the corresponding chloride by adding HCl. Subsequently the chloride is converted to the corresponding phosphate by adding $H_3PO_4$. The reaction solution is subsequently neutralized by adding a suitable base, preferably NaOH or KOH, and the catalyst is precipitated.

In a further preferred embodiment, the catalyst is precipitated by diluting the reaction solution particularly with water.

One aspect of the invention relates to the manufacture of heterogeneous catalysts according to the described method, particularly the manufacture of aluminum phosphate, boron phosphate, iron phosphate and zirconium phosphate.

Aluminum phosphate is especially preferred as heterogeneous catalyst for the method of the invention for the manufacture of furan compounds, particularly furfural and 5-hydroxymethylfurfural.

EXAMPLES

Catalysts

A metal oxide and/or transition metal oxides and/or semimetal oxides as well as the metal hydroxides and/or transition metal hydroxides and/or semimetal hydroxides are commercially available materials and have been purchased.

The metal phosphates and/or transition metal phosphates and/or semimetal phosphates were produced according to the methods of the invention, except for gallium phosphate, from the nitrates (Al, Fe), hydroxides (Al), oxides (Al), chlorides (Ti), and oxochlorides (Zr), acids (B).

Analytics

The aqueous reaction solutions were analyzed by means of quantitative HPLC-measurements. The measurement is carried out using an Agilent HPLC 1100 having a RID 1200 detector. In this respect the HPLC is loaded with $H_2SO_4$ (0.005 mol/l) using a flow rate of 0.6 ml/min at 50° C. The column is an Aminex 87H (300×7.8 mm), the pre-column is a Bio RAD 125-0129. D-fructose, D-glucose, D-xylose, 5-hydroxymethylfurfural and furfural are detected. In addition, formic acid, acetic acid, lactic acid and levulinic acid can occur due to the decomposition of the products in different amounts.

Batch Use

All tests for the manufacture of furan compounds according to a batch method were carried out in a 100 ml high pressure steal autoclave having an external heating element (Autoclave Engineers, USA). The reactor is equipped with a magnetic stirrer and a gas inlet valve. The reactor can be flushed via the gas inlet valve with an inert gas in order to avoid consecutive reactions with atmospheric oxygen at high temperatures.

Continuous Mode

All tests for the manufacture of furan compounds according to a continuous method were carried out in a 100 ml high pressure steal autoclave equipped with an external heater and at least one HPLC pump (JASCO, Germany). The synthesis installation is shown in FIG. 1. Mixing of water and saccharide solution occurs directly previous to the reactor vessel and thus allows for superior control of temperature and, therefore of the duration of the reaction. A sinter metal filter at the outlet of the high pressure steal autoclave prevents leakage of the catalyst which is dispersed in the reactor volume by means of a magnetic stir bar.

Synthesis of Aluminum Phosphate

The synthesis of aluminum phosphate is carried out via the precursor compound aluminum nitrate. The aluminum nitrate is at first dissolved in water, mixed with an excess of concentrated phosphoric acid and heated for 8 hours at 100° C. under reflux. Subsequently the formed aluminum phosphate is precipitated by adding ammonia and is filtrated. The filtrate is washed with water dried at 105° C. for 24 hours and subsequently calcinated for 4 hours at 400° C.

Synthesis of supported aluminum phosphate also is carried out via the precursor compound aluminum nitrate. The support material, particularly $\alpha$-$Al_2O_3$, is mixed with an aqueous aluminum nitrate solution. After 60 minutes an excess of concentrated phosphoric acid is added and is heated for 8 hours at 100° C. under reflux. Subsequently the aluminum phosphate is precipitated onto the soaked support material by means of addition of an overstoichiometric amount of ammonia, is washed with a sufficient amount of water, is dried at 105° C. for 24 hours and subsequently is calcinated for 4 hours at 400° C.

Manufacture of Furfural and 5-Hydroxymethyl Furfural

The method of the invention for the manufacture of furan compounds is examined for the manufacture of furfural and 5-hydroxymethylfurfural from xylose and fructose in the presence of various heterogeneous catalysts.

Comparative Example 1

Manufacture of Furfural from Xylose without Catalyst in Batch Mode 10 g xylose are combined under stirring with 190 g of completely desalinated water so that a solution of 5% xylose is obtained. 50 ml of the solution are added to a 100 ml reactor having an external heater. Subsequently the reactor is closed and is inertisized for 5 minutes with a nitrogen atmosphere. The reactor is adjusted to a preliminary pressure of 5 bar and a temperature of 160° C. Subsequently the reactor is heated. Once a temperature of 160° C. is reached in the reactor the reaction mixture is stirred with 305 rpm. After a reaction time of 60 minutes the heating device is removed and the reactor is cooled in air until the internal temperature is 40° C. Subsequently the excess pressure present in the internal of the reactor is released by means of a gas outlet in the reactor and the reactor is opened. The reaction solution is weighted and is analysed quantitatively in view of its ingredients using HPLC.

Comparative Example 2

The process is carried out as described in example 1; however, 500 mg aluminum phosphate ($AlPO_4$) in powder form is not added to the reactor but 2.5 ml 98% $H_2SO_4$ corresponding to a ratio of xylose to $H_2SO_4$ of 1:1.8.

Example 1

Manufacture of Furfural from Xylose Using $AlPO_4$ in Batch Mode 25 g xylose are combined with 475 g of completely desalinated water under stirring so that a solution of 5% xylose is obtained. 50 ml of the solution are added to a 100 ml reactor having an external heater. Subsequently 500 ml aluminum phosphate ($AlPO_4$) in powder form are added to the reactor. Subsequently the reactor is closed and is charged for 5 minutes with an nitrogen atmosphere. The reactor is adjusted to a preliminary pressure of 5 bar nitrogen and a temperature of 160° C. Subsequently the reactor is heated. Once a temperature of 160° C. is reached in the reactor the reaction mixture is stirred at 305 rpm. After a reaction time of 60 minutes the heating device is removed and the reactor is cooled in air until the internal temperature of the reactor is 40° C. Subsequently the excess pressure present inside the reactor is released by means of a gas outlet in the reactor and the reactor is opened. The reaction solution is weighted and the aluminum phosphate is separated using a folded filter (Whatman Grade 589). The aluminum phosphate is dried for 24 hours at 105° C. and is also weighted. The reaction solution is analyzed quantitatively in view of its ingredients using HPLC.

Examples 2 to 6

The process is carried out as described in example 1; however, not 500 mg aluminum phosphate ($AlPO_4$) in powder form are added to the reactor but:

500 mg aluminosilicate (5% $Al_2O_3$)   (example 2)
500 mg aluminosilicate (30% $Al_2O_3$)  (example 3)
500 mg aluminosilicate (40% $Al_2O_3$)  (example 4)
500 mg $Al_2O_3$                        (example 5)
500 mg $TiO_2$ (I)                      (example 6)

Examples 7 to 8

The process is carried out as described in example 1 with except for the reaction temperature which is increased in example 7 to 180° C. and in example 8 to 200° C. In addition, the reaction time is reduced to 30 minutes.

Table 1 summarizes the results for the manufacture of furfural from an aqueous xylose solution obtained with different heterogeneous catalysts in batch mode. Comparative examples are on the one hand the non-catalysed reaction (comparative example 1) and on the other hand the homogeneously catalysed reaction with $H_2SO_4$ (comparative example 2).

TABLE 1

Manufacture of furfural from xylose

|  | Catalyst | Temperature (° C.) | Reaction time (min) | Xylose turnover (%) | Furfural yield (%) |
|---|---|---|---|---|---|
| Comparative example 1 | without | 160 | 60 | 7.91 | 6.24 |
| Comparative example 2 | $H_2SO_4$ | 160 | 60 | 70.52 | 34.54 |
| Example 1 | $AlPO_4$ | 160 | 60 | 17.50 | 10.48 |
| Example 2 | aluminosilicate (5% $Al_2O_3$) | 160 | 60 | 84.64 | 16.75 |
| Example 3 | aluminosilicate (30% $Al_2O_3$) | 160 | 60 | 78.42 | 18.94 |
| Example 4 | aluminosilicate (40% $Al_2O_3$) | 160 | 60 | 54.52 | 15.49 |
| Example 5 | $Al_2O_3$ | 160 | 60 | 83.99 | 18.28 |
| Example 6 | $TiO_2$ (I) | 160 | 60 | 79.94 | 32.57 |
| Example 7 | $AlPO_4$ | 180 | 30 | 27.13 | 18.08 |
| Example 8 | $AlPO_4$ | 200 | 30 | 89.02 | 46.44 |

Manufacture of 5-Hydroxymethylfurfural from Fructose without Catalyst in Batch Mode.

Comparative Example 3

25 g fructose are combined under stirring with 475 g completely desalinated water so that a solution of 5% fructose is obtained. 50 ml of the solution are added to a 100 ml reactor having an external heater. Subsequently the reactor is closed and is charged for 5 minutes with a nitrogen atmosphere. The reactor is adjusted to a temperature of 180° C. Subsequently the reactor is heated. Once a temperature of 180° C. is reached in the reactor, the reaction mixture is stirred at 305 rpm. After a reaction time of 30 minutes the heating device is removed and the reactor is cooled in air until the internal temperature of the reactor is 40° C. Subsequently the excess pressure present inside the reactor is released by means of gas outlet present in the reactor and the reactor is opened. The reactor solution is weighted and is analyzed quantitatively in view of its ingredients using HPLC.

Comparative Example 4

25 g fructose are combined with 475 g completely desalinated water so that a solution of 5% fructose is obtained. 50 ml of the solution are added to a 100 ml reactor having an external heater. Subsequently 2.5 ml 98% $H_2SO_4$ are added to a reactor corresponding to a ratio of fructose to $H_2SO_4$ of 1:1.8. Subsequently the reactor is closed and is loaded for 5 minutes with a nitrogen atmosphere. The reactor is adjusted to a temperature of 180° C. Subsequently the reactor is heated. Once the temperature of the reactor reaches 180° C. the reaction mixture is stirred at 305 rpm. After a reaction time of 10 minutes the heating device is removed and the reactor is cooled in air until the internal temperature of the reactor is 40° C. Subsequently the excess pressure present in the reactor is released by means of a gas outlet in the reactor and the reactor is opened. The reaction solution is weighted. The reaction solution is analysed quantitatively in view of its ingredients using HPLC.

Manufacture of 5-Hydroxymethylfurfural from Fructose with Catalyst in Batch Mode Example 9

25 g Fructose are combined with 475 g completely desalinated water under stirring so that a 5% solution of fructose is obtained. 50 ml of the solution are added to 100 ml reactor having an external heater. Subsequently 500 mg aluminum phosphate ($AlPO_4$) in powder form are added to the reactor. Subsequently the reactor is closed and is loaded for 5 minutes with an nitrogen atmosphere. The reactor is adjusted to a temperature of 180° C. Subsequently the reactor is heated. Once a temperature of 180° C. is reached in the reactor the reaction mixture is stirred at 305 rpm. After a reaction time of 30 minutes the heating device is removed and the reactor is cooled in air until the internal temperature of the reactor is 40° C. Subsequently the excess pressure present inside the reactor is released by means of a gas outlet in the reactor and the reactor is opened. The reaction solution is weighted and the aluminum phosphate is separated by means of a folded filter (Whatman Grade 589). The aluminum phosphate is dried for 24 hours at 105° C. and is also weighted. The reaction solution is analyzed quantitatively in view of its ingredients using HPLC.

Examples 10 to 17

The process is carried out as described in example 9; however, not 500 mg aluminum phosphate ($AlPO_4$) in powder form are added to the reactor but:

500 mg $TiO_2$ (I)        (example 10)
500 mg SiAl (40%)         (example 11)
500 mg $FePO_4$           (example 12)
500 mg $Zr_3(PO_4)_4$     (example 13)
500 mg $ZrO_2$            (example 14)
500 mg $TiO_2$ (II)       example 15)
500 mg $GaPO_4$           (example 16)
500 mg $BPO_4$            (example 17)

Example 18

The process is carried out as described in example 9 except for the reaction temperature which is increased to 200° C. and the reaction time is reduced to 10 minutes.

Table 2 summarizes the results obtained in the manufacture of 5-hydroxymethylfurfural from an aqueous fructose solution using different heterogeneous catalysts in batch mode. The comparative examples are on the one hand the non-catalysed reaction (comparative example 1) and on the other hand homogeneously the catalysed reaction using $H_2SO_4$ (comparative example 2).

TABLE 2

Manufacture of 5-hydroxymethylfurfural

| | Catalyst | Temperature [° C.] | Duration [min] | Fructose turnover [%] | Yield HMF [%] |
|---|---|---|---|---|---|
| Comparative 3 | without | 180 | 30 | 69.69 | 39.50 |
| Comparative 4 | $H_2SO_4$ | 160 | 10 | 99.49 | 5.69 |
| Example 9 | $AlPO_4$ (400° C.) | 180 | 30 | 81.63 | 46.31 |
| Example 10 | $TiO_2$ (I) | 180 | 30 | 94.47 | 22.44 |
| Example 11 | aluminosilicate (40% $Al_2O_3$) | 180 | 30 | 79.31 | 23.93 |
| Example 12 | $FePO_4$ | 180 | 30 | 94.00 | 41.61 |
| Example 13 | $Zr_3(PO_4)_4$ | 180 | 30 | 86.81 | 40.40 |
| Example 14 | $ZrO_2$ | 180 | 30 | 74.48 | 45.46 |
| Example 15 | $TiO_2$ (II) | 180 | 30 | 79.23 | 46.36 |
| Example 16 | $GaPO_4$ | 180 | 30 | 75.11 | 43.48 |
| Example 17 | $BPO_4$ | 180 | 30 | 71.21 | 44.49 |
| Example 18 | $AlPO_4$ (400° C.) | 200 | 10 | 95.33 | 44.35 |

In the manufacture of furfural and 5-hydroxymethylfurfural in batch mode using the method of the invention high turnover numbers can be obtained, while using the homogeneously catalysed method comparable yields are obtained especially at a reaction temperature of 160° C. to 180° C. and a reaction time of 10 to 60 minutes. The turnover rates and yields obtained by means of the homogeneously catalysed method can be obtained with the method of the invention under equal reaction conditions, in particular using $TiO_2$. At a reaction temperature of 200° C. and a reaction time of 60 minutes yield and turnover rate of the homogeneously catalysed method even can be outperformed when $AlPO_4$ is used as heterogeneous catalyst for the manufacture of furfural from xylose.

In addition, it has been shown that in the manufacture of 5-hydroxymethylfurfural also increased turnover numbers can be achieved with the method of the invention which are significantly higher than in the homogeneously catalysed method. The yields obtained here are also significantly higher than in the homogeneously catalysed method, particularly at a reaction temperature of 180° C. and a reaction time of 30 minutes. The homogeneously catalysed method shows under mild reaction conditions very low turnover rates, while in the method of the invention high turnover rates and yields are obtained, particularly with $AlPO_4$ (400° C.), wherein $AlPO_4$ (400° C.) refers to an aluminum phosphate catalyst calcinated at 400° C.

The reaction temperature and the reaction time have a great influence on the obtained dehydration yields. In this respect results strongly varying from each other are obtained in ranges of 160° C. to 200° C. and 10 to 60 minutes.

Typically high yields are expected at short reaction times and high temperatures. The reaction parameters, especially the reaction temperature and reaction time as well as the educts used can readily applied to a synthesis installation in continuous mode.

Manufacture of 5-Hydroxymethylfurfural from Fructose with Catalyst in Continuous Mode The manufacture of 5-hydroxymethylfurfural from fructose in continuous mode is carried out in a synthesis installation having a stirrer vessel reactor according to FIG. 1. 140 g fructose are combined with 860 g of completely desalinated water under stirring so that a solution of 14% fructose is obtained which is loaded via one of the two strands of the synthesis installation through the installation to the mixing device and subsequently into the reactor. 1000 mg of aluminum phosphate ($AlPO_4$) in powder form are added to a 100 ml reactor (1) having an external heater and a free reactor volume of 70 ml. Cooling of the reactor output is carried out by means of a cooling system (17) having a temperature of ≤20° C. The aluminum phosphate is dispersed by means of a magnetic stirrer at 400 rpm in the reaction volume. The reactor (1) is adjusted by means of the pressure control valve (15) to a preliminary pressure of 50 bar and the heating device (16) is adjusted to a temperature of 190° C. For starting and flooding the installation 2.4 ml/min and 8.14 ml/min of completely desalinated water are loaded by means of the high pressure pumps (11) and (12) through the installation and into the reactor (1). The pre-heating device (13) is adjusted to 230° C. and the preheating device (14) is adjusted to 190° C. The heating device (16) arranged in front of the reactor inlet is adjusted to 165° C. and the external reactor heating is adjusted to 190° C. After 50 minutes a constant temperature of 190° C. is reached in the reactor. Subsequently the high pressure pump (11) is shifted to fructose solution. In this respect the high pressure pump (11) conveys 1.21 ml/min fructose solution and the high pressure pump (12) conveys 2.34 ml/min of completely desalinated water. At the reactor inlet (56) thus a fructose solution having a concentration of about 5% is present. The medium dwell time of the fructose solution in the reactor (1) is 17.5 minutes. After 81.09 minutes the reaction solution including the formed 5-hydroxymethylfurfural reaches the outlet of the installation. Now the formed product solution can continuously be removed at the outlet of the installation. For shutting down the installation the high pressure pump (11) is shifted to completely desalinated water, all pre-heaters are switched off and the installation is flushed and cooled for 90 minutes. The obtained product solution is weighted and the reaction solution is analyzed quantitatively in view of its ingredients using HPLC.

By means of further comparative examples using a reactor in continuous mode it has been shown that the reaction temperature and the reaction time has a great influence on the yields obtained in dehydrating fructose using various catalyst systems according to the invention. In this respect results strongly varying from each other are obtained in the ranges of 180° C. to 200° C. and 5 to 30 minutes using the various catalyst systems. The reaction parameter, especially reaction temperature and reaction time as well as the used educts and educt solutions can readily be applied to a synthesis installation which is not in continuous mode.

Calcination

Comparative examples for optimizing the method of the invention for the manufacture of a heterogeneous catalyst show that especially calcination is of importance for the activity of the resulting catalyst. FIG. 2 shows the influence of the calcinations temperature on the specific surface of the catalyst and the yields obtained therewith at equal reaction conditions. In this respect the specific surface of the $AlPO_4$ catalysts calcinated at various temperatures was determined by means of BET $N_2$ adsorptions isotherms. The optimal calcination temperature is in view of this between 400 and 600° C., especially between 450 and 550° C. based on the yield on 5-hydroxymethylfurfural. The specific surface of the catalyst is here between 130 and 160 $m^2/g$.

FIG. 3 shows that the catalytic activity of the $Zr_3(PO_4)_4$ catalyst is maintained even in case of repeated cycles showing a high lifecycle. This is especially interesting for industrial applications.

The manufacturing method of the invention is suitable for producing furan compounds, in particular furfural and 5-hydroxymethylfurfural, under mild reaction conditions from renewable primary products. The turnover numbers and yields of a homogeneously catalysed method can here be outperformed with the manufacturing method of the invention, wherein the process control is improved and the production costs are reduced. A further advantage of the method of the invention over the homogenously catalysed method is the significantly simplified recovery of the catalyst, especially in case of a reactor in continuous mode. Comparative tests show a strong influence of the reaction conditions on the obtainable turnover numbers and yields as well as in the manufacture of the catalyst and the manufacture of the furan compounds.

The invention claimed is:

1. Method for the manufacture of furfural and/or 5-hydroxymethylfurfural comprising the steps:
   (a) providing an aqueous saccharide solution,
   (b) adding to the solution a heterogeneous catalyst selected from the group consisting of $FePO_4$, $GaPO_4$, $BPO_4$, $Ti_3(PO_4)_4$ and $AlPO_4$,
   (c) heating the solution, and
   (d) separating the heterogeneous catalyst from the solution optionally using filtration.

2. Method according to claim 1, wherein the saccharide is xylose and/or fructose.

3. Method according to claim 2, wherein the saccharide is dehydrated.

4. Method according to claim 1, characterized in that the aqueous saccharide solution comprises at least one saccharide which is derived from a biogenic source or is obtained by means of a biorefining method.

5. Method according to claim 1, wherein the manufacture of furan compounds is carried out in batch mode or in continuous mode.

6. Method according to claim 1, wherein the heterogeneous catalyst has a specific surface in the range of from 100 to 200 $m^2/g$.

7. Method according to claim 1, wherein the heterogeneous catalyst is manufactured using a calcination step at a temperature of 400° C. to 1000° C.

8. Method according to claim 1, wherein the heterogeneous catalyst is not provided on a support or is provided on a support.

* * * * *